United States Patent [19]
Taylor et al.

[11] Patent Number: 5,831,062
[45] Date of Patent: Nov. 3, 1998

[54] USE OF THE HUMAN INTERFERON CONSENSUS GENE FOR GENE THERAPY

[75] Inventors: Milton W. Taylor, Bloomington, Ind.; Lawrence M. Blatt, Boulder, Colo.

[73] Assignee: Amgen Inc., Thousand Oaks, Calif.

[21] Appl. No.: 852,889

[22] Filed: May 8, 1997

Related U.S. Application Data

[60] Provisional application No. 60/017,220, May 9, 1996.
[51] Int. Cl.$^6$ .................................................... E07H 21/04
[52] U.S. Cl. ...................................... 536/23.52; 536/24.1
[58] Field of Search .............................. 435/6, 69.4, 91.4, 435/172.3, 320.1; 424/184.1, 93.21, 49; 514/44; 536/23.52, 24.1

[56] References Cited

FOREIGN PATENT DOCUMENTS 0 422 697 A1   4/1991   European Pat. Off. .
WO 93 21229   10/1993   WIPO .

OTHER PUBLICATIONS

Zang, et ala., "Gene Therapy with an Adeno–Associated Virus Carrying an Interferon Gene Results in Tumor Growth Suppression and Regression", Cancer Gene Therapy, vol. 3, No. 1, Jan. 1, 1996–Feb. 1996, pp. 31–38.

Zang, et al., "Treatment of a Human Breast Cancer Xenograft with an Adenovirus Vector Containing an Interferon Gene Results in Rapid Regression Due to Viral Oncolysis and Gene Therapy", Proceedings of the National Academy of Sciences, USA, vol. 93, Apr. 1996, pp. 4513–4518.

Hu, et al., "Loss of Oncogenic Potential of Tumor Cells Following Transduction with the Consensus IFN Gene in an AAV Vector", Journal of Cellular Biochemistry, vol. 0, No. 21A, 1995, p. 422.

Taylor, et al., "Targeting of Human Tumors in Nude Mice with Adenovirus–Associated Vectors Containing the Human Consensus Interferon Gene", 25$^{th}$ Annual Meeting of the International Society for Experimental Hematology, vol. 23–27, Aug. 1996, New York, New York, USA.

Mackenson et al. Immunostimulatory cytokines in somatic cells and gene therapy of cancer. Cytokine and Growth factor reviews vol. 8(2):119–128,Aug. 11, 1997.

Vieillard et al. Autocrine interferon–beta synthesis for gne therapy of HIV infection: increased resistance to HIV–1 in lymphocytes from healty and HIV–infected individuals. AIDS vol. 9:1221–1228., Nov. 02, 1995.

Glapsy et al. Treatment of hairy cell leukemia with a novel recombinant type–1 interferon, consensus interferon, and granulocyte colony–stimulating factor. J. IFN. Rsch. vol. 12, S1:575, Oct. 07, 1992.

Cao et al. Treatment of human hepatocellular carcinoma by fibroblast–mediated human interferon alpha gene therapy in combination with adoptive chemoimmunotherapy. J. Cnacer Res. Clin. Oncol. vol. 121:457–462, Aug. 17, 1995.

Orkin et al. Report and recommendations to the panel to assess teh NIH investments in research on gene therapy., Dec. 07, 1995.

Ferrantini et al. IFN–alpha 1 gene expression into a metastatic murine adenocarcinoma (TS/A) results in CD8+ T cell–mediated tumor rejection and development of antitumor immunity. J. Immunol., 153:(10):4604–4615, Nov. 1994.

*Primary Examiner*—James Ketter
*Assistant Examiner*—William Sandalis
*Attorney, Agent, or Firm*—Craig A. Crandell; Steven M. Odre; Ron K. Levy

[57] ABSTRACT

The present invention relates generally to a human interferon consensus gene useful for expression in eucaryotic systems and gene therapy. In particular, the present invention relates to treatment of cancer and cell proliferation disorders through use of viral vectors to deliver and express the human interferon consensus gene in the cells and/or tumors of a patient.

2 Claims, 5 Drawing Sheets

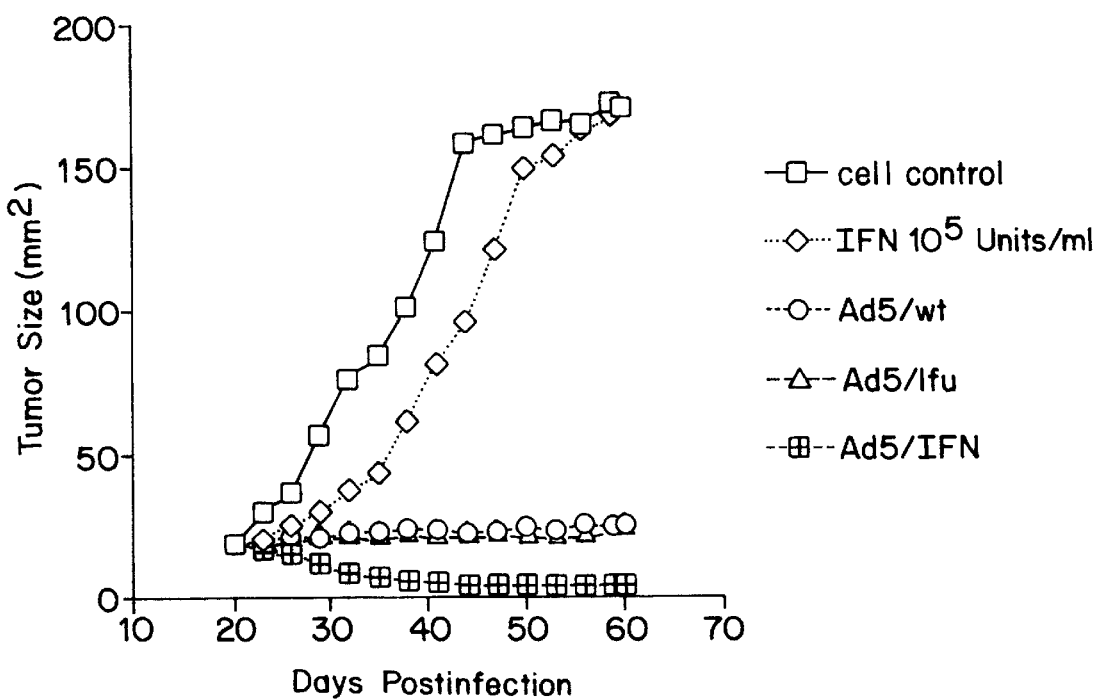
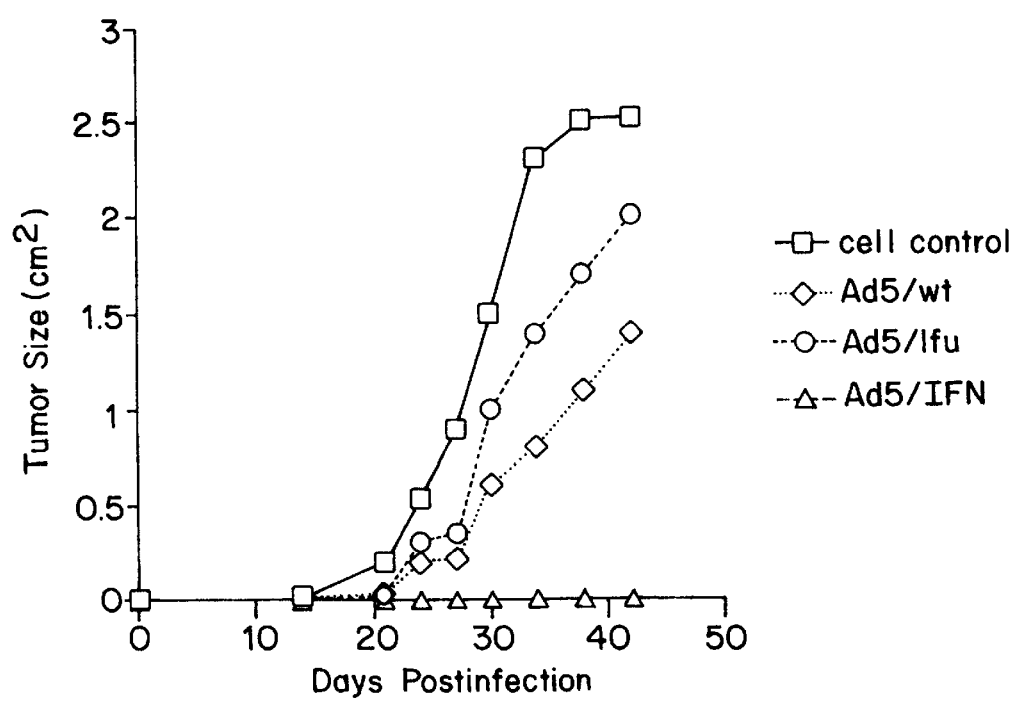

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 498 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TGTGATTTAC   CTCAAACTCA   TTCTCTTGGT   AACCGTCGCG   CTCTGATTCT   GCTGGCACAG           60
ATGCGTCGTA   TTTCCCCGTT   TAGCTGCCTG   AAAGACCGTC   ACGACTTCGG   CTTTCCGCAA          120
GAAGAGTTCG   ATGGCAACCA   ATTCCAGAAA   GCTCAGGCAA   TCTCTGTACT   GCACGAAATG          180
ATCCAACAGA   CCTTCAACCT   GTTTTCCACT   AAAGACAGCT   CTGCTGCTTG   GGACGAAAGC          240
TTGCTGGAGA   AGTTCTACAC   CGAGCTGTAT   CAGCAGCTGA   ACGACCTGGA   AGCATGCGTA          300
ATCCAGGAAG   TTGGTGTAGA   AGAGACTCCG   CTGATGAACG   TCGACTCTAT   TCTGGCAGTT          360
AAAAAGTACT   TCCAGCGTAT   CACTCTGTAC   CTGACCGAAA   AGAAATATTC   TCCGTGCGCT          420
TGGGAAGTAG   TTCGCGCTGA   AATTATGCGT   TCTTTCTCTC   TGAGCACTAA   CCTGCAGGAG          480
CGTCTGCGCC   GTAAAGAA                                                              498
```

( 2 ) INFORMATION FOR SEQ ID NO:2:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
AATTCCACCA   TGGCCTTGTC   CTTTTCTTTA   CACTGATGGC   CCTGCTGGTG   CTCAGCTACA           60
AGTCAACTCG   CTCTCTGGGC   TGTGATTTAC   CTCAAACTCA   TTCTCTTG                         108
```

( 2 ) INFORMATION FOR SEQ ID NO:3:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GTTACCAAGA  GAATGAGTTT  GAGGTAAATC  ACAGCCCAGA  GAGCAGATTG  ACTTGTAGCT    60
GAGCACCAGC  AGGGCCATCA  GTAAAGAAAA  GGACAAGGCC  ATGGTGG                  107
```

( 2 ) INFORMATION FOR SEQ ID NO:4:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
AATTCCACCA  TGGCCTTGTC  CTTTTCTTTA  CTGATGGCCC  TGCTGGTGCT  CAGCTACAAG    60
TCAATCTGCT  CTCTGGGC                                                      78
```

( 2 ) INFORMATION FOR SEQ ID NO:5:

( i ) SEQUENCE CHARACTERISTICS:
        ( A ) LENGTH: 587 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
AATTCCACCA  TGGCCTTGTC  CTTTTCTTTA  CTGATGGCCC  TGCTGGTGCT  CAGCTACAAG    60
TCAATCTGCT  CTCTGGGCTG  TGATTTACCT  CAAACTCATT  CTCTTGGTAA  CCGTCGCGCT   120
CTGATTCTGC  TGGCACAGAT  GCGTCGTATT  TCCCCGTTTA  GCTGCCTGAA  AGACCGTCAC   180
GACTTCGGCT  TTCCGCAAGA  AGAGTTCGAT  GGCAACCAAT  TCCAGAAAGC  TCAGGCAATC   240
TCTGTACTGC  ACGAAATGAT  CCAACAGACC  TTCAACCTGT  TTTCCACTAA  AGACAGCTCT   300
GCTGCTTGGG  ACGAAAGCTT  GCTGGAGAAG  TTCTACACCG  AGCTGTATCA  GCAGCTGAAC   360
GACCTGGAAG  CATGCGTAAT  CCAGGAAGTT  GGTGTAGAAG  AGACTCCGCT  GATGAACGTC   420
GACTCTATTC  TGGCAGTTAA  AAAGTACTTC  CAGCGTATCA  CTCTGTACCT  GACCGAAAAG   480
AAATATTCTC  CGTGCGCTTG  GGAAGTAGTT  CGCGCTGAAA  TTATGCGTTC  TTTCTCTCTG   540
AGCACTAACC  TGCAGGAGCG  TCTGCGCCGT  AAAGAATAAT  AGGATCC                  587
```

USE OF THE HUMAN INTERFERON CONSENSUS GENE FOR GENE THERAPY

This application claims the benefit of U.S. Provisional Application No. 60/017,220, filed May 9, 1996.

BACKGROUND OF THE INVENTION

Advances in molecular cloning techniques have led to the identification and isolation of an expanding array of genes with mutations responsible for human diseases. Such advancements have made it possible to consider gene therapy as a potential treatment for certain genetic and/or acquired disorders. Gene therapy is a set of approaches to the treatment of human disease based on the transfer of genetic material (DNA) into an individual. Gene therapy differs from conventional medical therapy in that it attempts to treat disease in an individual patient via administration of DNA rather than a drug.

The earliest applications of this approach dealt primarily with genetic diseases; the idea being that because many diseases are linked to the abnormal expression of a single gene, the expression of a normal gene artificially introduced into the right cells should be enough to make up for the deficiency. More recently, the possible indications of gene therapy have been extended to treatment of infectious diseases (e.g. AIDS), multifactorial disorders (e.g. diabetes, coronary heart disease), and cancer.

Cancer has been established as a genetic disease at the cellular level, and cancers arise through a multistage process driven by inherited and relatively frequent somatic mutation of cellular genes, followed by clonal selection of variant cells with increasingly aggressive growth properties. The therapeutic genes for cancer gene therapy include tumor suppressor genes (such as p53), cytokine genes, MHC class I gene, suicide genes, the multiple drug resistance gene, toxins, antisense and ribozymes. At least three important classes of genes-protooncogenes, tumor suppressor genes, and DNA repair genes-are targeted by mutations. Because the majority of mutations that contribute to cancer are somatic, introduction into cancer cells of a gene which might alter or inhibit the malignant phenotype is an intriguing and appealing concept.

Direct modification of tumor cells using cytokine genes to enhance host immunity has been studied extensively in various animal and human models over the past several years, and tumor cell-targeted gene therapy has recently received particular consideration as a potential alternative to systemic administration of cytokines in cancer therapy. Studies have involved transfer of genes for cytokines to cancer cells either outside the body (ex vivo) or directly into the patient (in vivo) in an attempt to stimulate immune recognition of not only the gene-modified cancer cells, but also cancer cells that have not received the gene and are situated elsewhere in the body.

Many cytokines have been examined for their efficacy in tumor cell-targeted gene therapy in different tumor models; Colombo and Forni, *Immunol. Today*, 15:48–51 (1994), and the expression of cytokine genes by tumor cells as a result of gene transfer has emerged as a novel strategy to augment in vivo host reactivity to various cancers; Tepper and Mule, *Human Gene Therapy*, 5:153–164 (1994) and references cited therein. Moreover, cytokine gene transfer into tumor cells is now regarded as an effective approach for the induction of systemic immunity against the unmodified parental tumor; Anderson, W. F., *Human Gene Therapy*, 5:1–2 (1994).

Type I (IFN-α, IFN-β, IFN-con) and type II (IFN-γ) interferons are a few of the cytokines which have been tested in various cancer gene therapy models. Type I interferons are well known growth inhibitory cytokines and are currently approved in the U.S. and other countries for the treatment of a variety of cellular proliferation disorders frequently associated with cancer. Such disorders include, but are not limited to, hairy cell leukemia, chronic myelogenous leukemia, multiple myeloma, malignant melanoma, Kaposi's Sarcoma and other leukemias.

Based upon the fact that deletions or mutations of type I interferon genes often occur in various primary human tumors and culture tumor cells (Diaz et al., *Proc. Natl. Acad. Sci. USA*, 85:5259–5263 (1988)), it has also been hypothesized that type I interferons may represent a new class of tumor suppressor; Lengyel, P., *Proc. Natl. Acad. Sci. USA*, 90:5892–5894 (1990). The hypothesis is difficult to test, however, partly because of the diversity of the human type I interferon system, and also because the therapeutic efficacy of interferon is still limited. These limitations include the length and frequency of treatment and severe side effects, which often accompany large amounts of interferon required for efficient reduction of tumor mass. For interferons to be effective in cancer gene therapy models, such limitations must be addressed, and efficient gene transfer techniques utilized.

Treatment of human breast cancer by conventional means has had rather limited success and attempts have been made to treat human breast cancer with type I and type II interferons. Unfortunately, the results of such studies have been disappointing; Repetto et al., *J. Biol. Regul. Homeost. Agents*, 7:109–114 (1993). IFN treatment of human breast cancers did enhance estrogen receptors and thus may be a useful agent in combination with tamoxifen; Josui et al., *Jpn. J. Cancer Res.*, 83:1347–1353 (1992); Seymour and Bezwoda, *Br. J. Cancer*, 68:352–356 (1993). Although preclinical studies have shown that many human breast cancer cell lines are sensitive to the antiproliferative effect of the type I interferons, appropriate gene therapy clinical protocols have not been developed for in vivo treatments.

Clearly, an efficacious and workable interferon-based in vivo gene therapy protocol would be of tremendous benefit to patients suffering from, and physicians treating, cancer.

SUMMARY OF THE INVENTION

The present invention is thus directed toward a method of treating cancer and other cell proliferation disorders by gene therapy. In particular, the present invention is directed towards the treatment of a variety of different tumors, e.g. breast cancers, using a nucleic acid construct comprising an expression control sequence and an human interferon consensus gene which is operatively linked to said expression control sequence, wherein the nucleic acid construct is capable of eliciting efficient and constant expression of the gene over a long period of time. Surprisingly, production of endogenous IFN-con through the use of a viral vector to integrate the IFN-con gene into a series of tumor cell lines, led to the inhibition of tumor growth in vitro and in vivo and to alteration of the genotype of the cells, thus providing a useful human cancer gene therapy model.

Also provided herein is a novel DNA signal sequence which encodes a polypeptide cleavable by eucaryotic cells and useful in effecting the expression of a gene operatively linked thereto in eucaryotic systems.

The IFN-con of the present invention is a synthetic nonnaturally-occurring polypeptide having antiproliferative activity. Preferably, IFN-con is a polypeptide having the amino acid sequence of IFN-con$_1$, IFN-con$_2$, or IFN-con$_3$. Most preferably, IFN-con has the amino acid sequence of IFN-con$_1$ and is equipped with the appropriate signal sequence to allow for expression in eucaryotic systems. Also comprehended by the invention are pharmaceutical compositions involving effective amounts of the nucleic acid constructs together with a pharmaceutically acceptable delivery vehicle including suitable diluents, buffers and adjuvants.

BRIEF DESCRIPTION OF THE DRAWINGS

FIG. 4 is a graph depicting the effects of Ad5/wt, recombinant viruses Ad5/lfu and Ad5/IFN, and IFN-con$_1$ on growth of MDA-MB-435 breast carcinoma in athymic nude mice. The mice were treated with IFN-con$_1$ or recombinant viruses at 3-day intervals starting at day 20 post infection.

FIG. 5 is a graph depicting the effects of Ad5/wt, and recombinant viruses Ad5/lfu and Ad5/IFN, on growth of K562 myelogenous leukemia cells in athymic nude mice. The mice were treated with the recombinant viruses on day 1 post infection.

DETAILED DESCRIPTION

Figure 1:
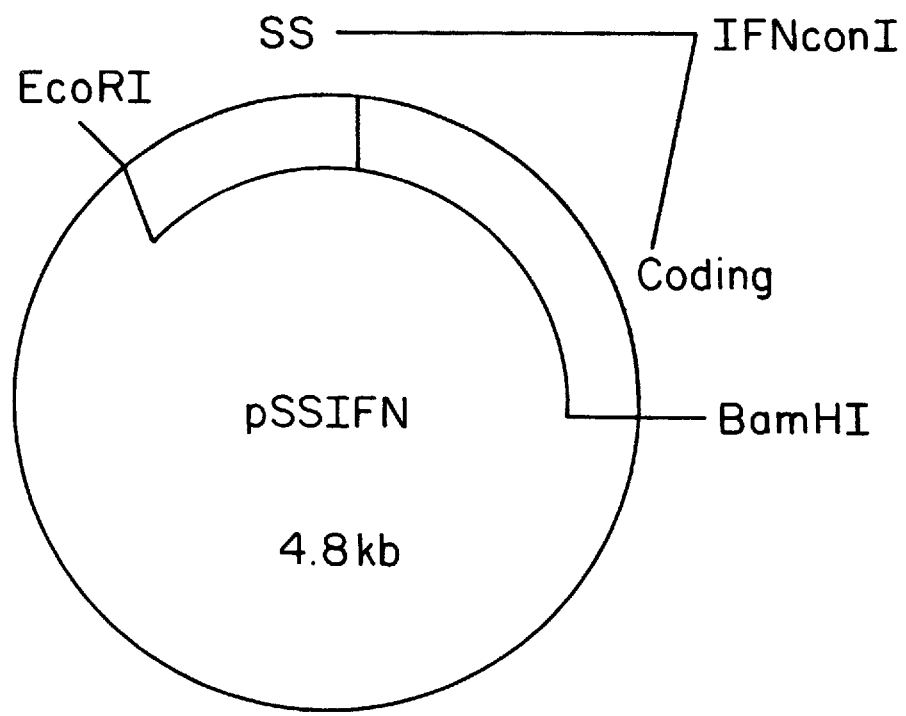
FIG. 1 depicts the pIFNSS plasmid containing the novel signal sequence (SS) and the coding sequence of IFN-con$_1$.

Traditional gene therapy approaches utilize ex vivo gene transfer; Liebert et al., *Human Gene Therapy*, 2:251–256 (1991). Ex vivo approaches involve transformation of cells in vitro with DNA (the cells having first been harvested from the patient and grown in culture), followed by introduction of the transformed cells back into the patient. In such techniques, in vitro transfer is generally done using retrovirus-based vectors; Zwiebel et al., *Science*, 243: 220–222 (1989). The advantages of the retrovirus-based vectors include:
1) the ability to transfer genes efficiently into cells that may be difficult to achieve by other methods;
2) the ability to infect a wide range of cell types;
3) the stable and precise integration of the foreign gene(s) carried by the vector into the target cells; and
4) lack of toxicity of the vectors in infected cells.

Suitable retroviruses for the practice of the present include, for example, LXSN and LNCX.

Adeno-associated viral (AAV) vectors have also been utilized for in vitro and in vivo transfer. AAV is an attractive candidate as a gene therapy vector in mammalian cells for the following reasons: 1) no disease has been associated with AAV in humans; 2) integration of wild type AAV into the host genome is relatively site-specific (within a small region of human chromosome 19) which could alleviate the risk of insertional mutations; 3) AAV is able to integrate into nondividing cells and the integrated provirus is generally stable; and 4) AAVs are remarkably stable and tolerate harsh experimental treatment. Suitable AAVs for the practice of the present include, for example, AAV-2 in the presence of various helper viruses such as dl3-94, psu201 and pWP-19.

Adenovirus vectors have been used successfully for in vivo gene transfer of the human cystic fibrosis transmembrane conductance regulator; Rosenfeld et al., *Cell*, 68:153–155 (1992), the ornithine transcarbamylase; Stratford et al., *Hum. Gene Therapy*, 1:241, 56 (1990), and factor IX; Smith et al, *Nat. Genet.*, 5:397, 402 (1993), among others. Adenoviruses have many advantages over other viruses for gene therapy in that high titers of virus can be obtained, the virus is stable and easy to handle, and the virus infects non-dividing cells; Callaud et al., *Eur. J. Neurosci.*, 5:1287, 91 (1993).

Any of the above-mentioned viral vectors, as well as other replication-defective and replication-competent viral vectors can be used as the vehicle to deliver and express IFN-con in the methods of the present invention. Moreover, the interferon-containing viral vectors may be used in human studies which involve direct application or which involve ex vivo transduction of lymphocytes, other tumor cells, or stem cells. In one embodiment of the present invention, an adenovirus vector, adenovirus-5, is chosen as the vehicle to deliver and express IFN-con via direct in vivo application. The final construct can be made with the IFN-con gene inserted in any of several regions of the adenovirus vector.

As employed herein, human interferon consensus (IFN-con) means a nonnaturally-occurring polypeptide, which predominantly includes those amino acid residues that are common to a subset of IFN-α's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not extant in that position in at least one naturally-occurring subtype. IFN-con encompasses but is not limited to the amino acid sequences designated IFN-con$_1$, IFN-con$_2$ and IFN-con$_3$ which are disclosed in commonly owned U.S. Pat. Nos. 4,695,623 and 4,897,471, the entire disclosures of which are hereby incorporated by reference. DNA sequences encoding IFN-con may be synthesized as described in the above-mentioned patents or other standard methods. In a preferred embodiment of the present invention, the IFN-con sequence is IFN-con$_1$ (SEQ ID NO:1)

Interferons exert their effects through receptors at the cell surface. IFNs produced in high eucaryotic cells must be secreted and bound subsequently to their receptor to function biologically. The secretion of the protein is dependent upon the signal sequence prior to the coding sequence of the molecule. Since the IFN-con$_1$ DNA in the bacterial vector does not contain the signal sequence, the first step to build eucaryotic expression vectors of IFN-con$_1$ was to generate that sequence. The signal sequence will encode a polypeptide capable of being cleaved by eucaryotic cells. In the present invention, two complementary oligos were designed to encode the amino acid residues in the signal peptide that are common to all naturally occurring human IFN-α subtypes (consensus). The actual construction of this novel signal sequence is described in Example 1 below.

The general approaches for the construction of eucaryotic expression vectors of a given gene include isolation of the desired DNA insert which can then be incorporated into an expression vector in that control of expression is driven by a promoter/regulator sequence existing in the vector. It may be preferred that a recombinant vector construct not become integrated into the host cell genome of the patient or mammalian subject, and therefore, it may be introduced into the host as part of a non-integrating nucleic acid construct. A coding sequence is "operatively linked to" or "under the control of" the expression control system in a cell when DNA polymerase will bind the promoter sequence and transcribe the erythropoietin-encoding sequence into mRNA. Thus, the nucleic acid construct includes a DNA sequence which encodes a polypeptide directly responsible for a therapeutic effect, as well as a sequence(s) controlling the expression of the polypeptide.

To construct synthetic genes for expression of human IFN-con$_1$ in eucaryotic cells, the choice of promoters that drive the expression of IFN is critical. The promoters selected for use must be selected with the knowledge of level of expression and tissue specificity. In general, a promoter that can function in a variety of eucaryotic cells with high efficiency is the first choice. Examples of such promoters include cytomegalovirus (CMV) and Rous sarcoma virus long terminal repeat (RSV-LTR). However, if high level of expression is not necessarily beneficial (as might be the case at times with IFN due to its cytotoxic effects on cell growth), there are other promoters, e.g., mouse mammary tumor virus (MMTV)LTR and mouse metallothionein-1 (mMT-1), which are inducible and constitutive expression without induction is often low. Also included are certain housekeeping gene promoters which are constitutively expressed but at low levels. Finally, in addition to a promoter, a polyadenylation (poly A) signal downstream of the coding sequence is also required for polyadenylation of transcribed mRNAs.

The cells targeted for gene transfer in accordance with the present invention include any cells to which delivery of the interferon consensus gene is desired. Disorders targeted for gene therapy with the IFN-con viral vectors described in the present invention include those disorders for which interferons are known to be effective. For example, IFN-con is effective in treating cell proliferation disorders frequently associated with cancer. Such disorders include, but are not limited to, hairy cell leukemia, chronic myelogenous leukemia, multiple myeloma, malignant melanoma, Kaposi's Sarcoma and other leukemias. In addition, viral conditions treatable by IFN-con include, but are not limited to, hepatitis A, hepatitis C, other non-A, non-B hepatitis, hepatitis B, herpes virus (EB, CML, herpes simplex), papilloma, poxvirus, picorna virus, adeno virus, rhino virus, HTLV I, HTLV II, and human rotavirus.

When used a therapeutic, a therapeutically effective dosage of the vectors will be administered for a therapeutically effective duration. By "therapeutically effective duration" and "therapeutically effective amount" is meant an amount and duration sufficient to achieve a selected desired result without undue adverse effects, and such amounts and duration can be readily determined by those skilled in the medical arts treating the various diseases.

The formulations suitable for administration of the viral vectors of the present invention will include aqueous and non-aqueous isotonic sterile injection solutions and suspensions. It will be appreciated that the administration of the vectors will be by procedures well known to those skilled in the pharmaceutical arts, e.g., direct delivery to the target tumor or cell, intranasally, intravenously, intramuscularly, subcutaneously, and through oral administration, either alone or in combination.

The following examples are offered to more fully illustrate the invention, but are not to be construed as limiting the scope thereof. Example 1 describes the construction of the plasmids and recombinant viruses used in Examples 2–8 of the present invention. Example 2 describes a study wherein a human breast ductal carcinoma cell line was treated with various recombinant viruses or IFN-con$_1$ shortly after transplantation into athymic nude mice. Example 3 describes a study wherein established MDA-MB-435 tumors were treated with various recombinant viruses. Example 4 describes a study wherein K562 cells, a myelogenous leukemic cell line known to form large tumors in vivo (within one week of transplantation into athymic nude mice) and known to be quite resistant to IFN in vitro (see Example 6) were treated with various recombinant viruses shortly after transplantation. Example 5 describes a study wherein RPMI 1846 cells, a fast growing hamster melanoma which develops into a tumor in Syrian hamsters, were treated with various recombinant viruses shortly after transplantation. Example 6 describes a study wherein the in vitro effects of each of the recombinant adenovirus viruses on MDA-MB-435 cell growth, K562 cell growth, and RPMI 1846 cell growth was evaluated. In Example 7, the amount of IFN-con$_1$ being produced by infected cells was measured from 6 to 72 hours after infection in vitro every 6 hours. Example 8 provides histological analysis of control and treated breast tumors. And finally, Example 9 provides the results obtained when AAV/IFN-con viral vectors were used to infect a number of other human tumor cell lines.

EXAMPLE 1

This example describes the construction of the plasmids and recombinant viruses used in the methods of the present invention.

Plasmids

Standard cloning techniques were used to construct the plasmids. The construction of a bacterial expression vector (pIFN-α) containing a DNA fragment corresponding to the coding region of IFN-con$_1$ is described in Alton et al., *In: The biology of the interferon system* (ed De Maeyer, Schellekens) pgs. 119–128. Elsevier, Amsterdam (1983), the disclosure of which is herein incorporated by reference. In order to construct vectors capable of expressing IFN-con in eucaryotic systems, two complementary oligonucleotides, oligos 1 and 2, were designed to encode a signal peptide whose amino acid residues are common to naturally occurring human IFN-α subtypes. The oligonucleotide sequence, oligo 1 (SEQ ID NO:2) is as follows:

```
5' AATTCCACCATGGCCTTGTCCTTTTCTTTACACTGATGGCCCT
   GCTGGTGCTCAGCTACAAGTCAACTCGCTCTCTGGGCTGTGAT
   TTACCTCAAACTCATTCTCTTG 3'
```

The oligonucleotide sequence, oligo 2 (SEQ ID NO:3) is as follows:

```
5' GTTACCAAGAGAATGAGTTTGAGGTAAATCACAGCCCAGAGAGCA
   GATTGACTTGTAGCTGAGCACCAGCAGGGCCATCAGTAAAGAAAG
   GACAAGGCCATGGTGG
```

These oligonucleotides were synthesized and assembled by standard methods. The double stranded oligonucleotide was then assembled by taking one nanomole of either oligo 1 or 2 and subjecting to 5'-phosphorylation in the presence of T4 kinase and ATP at 37° C. for 60 minutes. Annealing was carried out by mixing the phosphorylated oligos 1 and 2 together, warmed to 85° C. for 2 minutes, then 65° C. for 15 minutes, room temperature for 15 minutes and on ice for 15 minutes. The resulting novel duplex strands (SS fragment) (SEQ ID NO:4) includes the codon for an initiator methionine and twenty-two other amino acids of consensus signal peptide. It also contains a Kozak consensus (CCA/GCCATGG) upstream of ATG. The Kozak sequence has been shown to be important for high efficiency of translational initiation in eucaryotic cells. In addition, EcoRI restriction site at the 5'-end and the BstEII site at the 3'-end in the fragment permits its easy insertion into pIFN-α. The SS fragment was then incorporated in a position prior to the coding region of IFN-con$_1$ by cleaving pIFN-α with EcoRI and BstEII, followed by insertion of the SS fragment (with EcoRI and BstEII ends) into those two sites to generate pIFNSS (FIG. 1). With this incorporation, the trp promoter/operator and Shine Delgarno sequences from the bacterial vector pIFN-α are eliminated. The 0.6-kb EcoRI/BamHI fragment coding for the signal peptide and entire coding sequence of the IFN-con$_1$ is as follows (SEQ ID NO:5):

```
5' AATTCCACCATGGCCTTGTCCTTTTCTTTACTGATGGCCCT
   GCTGGTGCTCAGCTACAAGTCAATCTGCTCTGTGTGAT
   TTACCTCAAACTCATTCTCTTGGTAACCGTCGCGCTCTHATTC
   TGCTGGCACAGATGCGTCGTATTTCCCCGTTTAGCTGCCTGAA
   AGACCGTCACGACTTCGGCTTTCCGCAAGAAGAGTTCGATGGC
   AACCAATTCCAGAAAGCTCAGGCAATCTCTGTACTGCACGAAA
   TGATCCAACAGACCTTCAACCTGTTTTCCACTAAAGACAGCTC
   TGCTGCTTGGGACGAAAGCTTGCTGGAGAAGTTCTACACCGAG
   CTGTATCAGCAGCTGAACGACCTGGAAGCATGCGTAATCCAGG
   AAGTTGGTGTAGAAGAGACTCCGCTGATGAACGTCGACTCTAT
   TCTGGCAGTTAAAAAGTACTTCCAGCGTATCACTCTGTACCTG
   ACCGAAAAGAAATATTCTCCGTGCGCTTGGGAAGTAGTTCGCG
   CTGAAATTATGCGTTCTTTCTCTCTGAGCACTAACCTGCAGGA
   GCGTCTGCGCCGTAAAGAATAATAGGATCC 3'
```

The Ad5/IFN plasmid was then generated by inserting the 0.6-kb fragment from pIFNSS into the XbaI site of the pFG-dx1 by blunt end ligation. Restriction fragments used for ligation were purified from agarose gels using GENECLEAN (BIO 101). PFG-dx1 contains 40% of the right end of the adenovirus genome with a deletion from 78.5 to 84.7 map units. This 1.9-kb deletion removes most of the E3 region but leaves the E3 promoter and termination site. 293 cells (a human embryonic kidney cell line transformed with the left end of the adenoviral genome and containing the adenovirus E1a and E1b genes) were cotransfected with the plasmid Ad5/IFN and EcoRI digested adenovirus-5 DNA to rescue the recombinant virus; Wang & Taylor, *Mol. Cell. Biol.*, 13:918–927 (1993), which was plaque purified twice and analyzed by restriction enzyme digestion.

Adenovirus-5 wildtype (Ad5/wt) and Ad5-Luc3 (Ad5/lfu) were obtained from F. Graham (Hamilton, ON, Canada). Ad5-Luc3 contains the luciferase gene flanked by the simian virus 40 regulatory sequences in the E3 region of the adenovirus.

Recombinant Viruses

Ad5/wt, Ad5/lfu, and Ad5/IFN were added to monolayers of 293 cells at a multiplicity of infection (moi) of 50. The cells and media were harvested 2 to 3 days after infection and virus was released by sonication. Cell debris was removed by centrifugation and the clarified lysate carefully layered over CsCl (1.43 g/cm$^3$) and centrifuged in a Beckman SW-28 rotor at 20,000 rpm for 1 hour at 4° C. The visible virus band was collected and adjusted to 1.34 g/cm$^3$, mixed with three times volume CsCl (1.34 g/cm$^3$), and then centrifuged at 30,000 rpm for 24 hours. The resulting band of virus was collected and dialyzed against two changes of 200 vol 10 mM TrisHCl/1 mM EDTA at 4° C. for 4 hours. The purified virus was diluted in tris-saline-glycerol and stored at −70° C. The titer of the virus stocks were determined by plaque assay on 293 cells.

EXAMPLE 2

This example describes a study wherein MDA-MB-435 cells, a human breast ductal carcinoma cell line, were treated with various recombinant viruses or IFN-con$_1$ shortly after transplantation into athymic nude mice.

MDA-MB-435 cells were injected into the breast area of 3- to 4-week-old female athymic BALB/c mice (Harlan-Sprague-Dawley) at a concentration of 1×10$^6$ cells per mouse. On the following day, either IFN-con$_1$ (10,000 units or 100,000 units), wild-type adenovirus (Ad5/wt) (1×10$^8$ plaque forming units (pfu) per recombinant virus), recombinant adenovirus containing the IFN-con$_1$ gene (Ad5/IFN) (1×10$^8$ pfu), recombinant adenovirus containing the luciferase gene (Ad5/lfu) (1×10$^8$pfu), or PBS (100 μl) were injected into the same area, and then tumor growth evaluated for 60 days.

Figure 2:
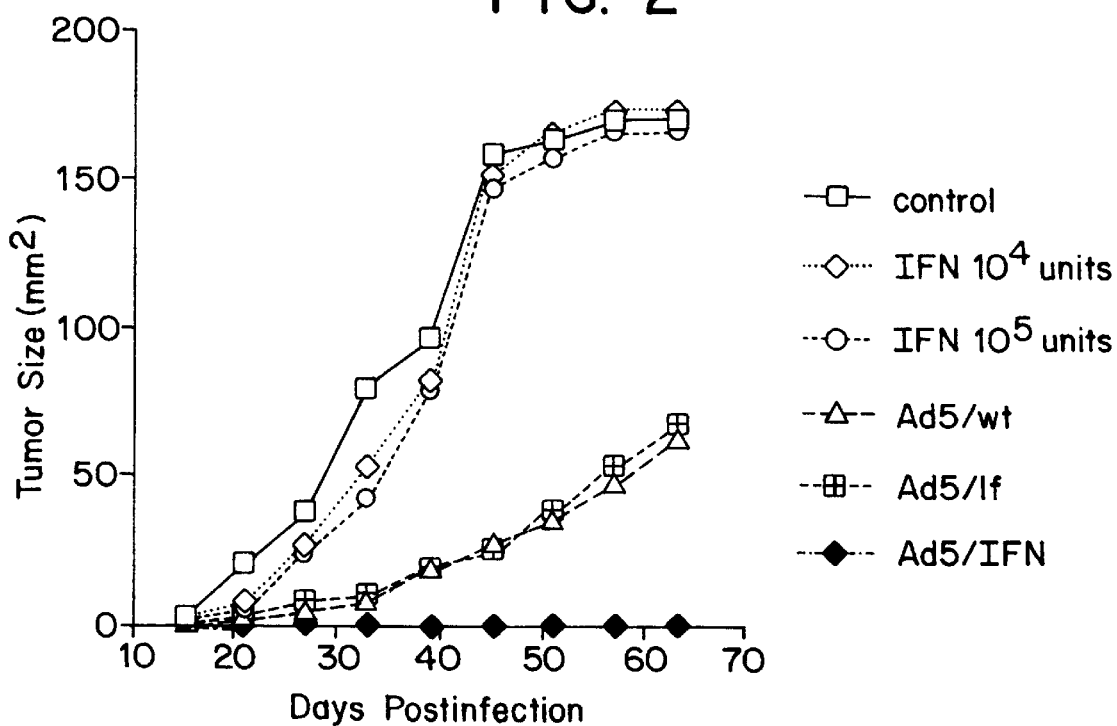
FIG. 2 is a graph depicting the effects of Ad5/wt, recombinant viruses Ad5/lfu and Ad5/IFN, and IFN-con$_1$ on growth of MDA-MB-435 breast carcinoma in athymic nude mice. The mice were treated with IFN-con$_1$ or recombinant viruses one time on day 1 post infection.

As depicted in FIG. 2, there was no visible growth of tumors when mice were injected with Ad5/IFN. Tumors treated directly with IFN-con$_1$ grew significantly slower than control tumors, but by day 45, there was no significant difference between those treated with either IFN-con$_1$ and controls. Mice that were infected with wild-type adenovirus or a replication competent recombinant adenovirus containing the luciferase gene, produced smaller tumors that grew significantly slower than the tumors in control animals.

EXAMPLE 3

This example describes a study wherein established MDA-MB-435 tumors were treated with various recombinant viruses.

Figure 3:
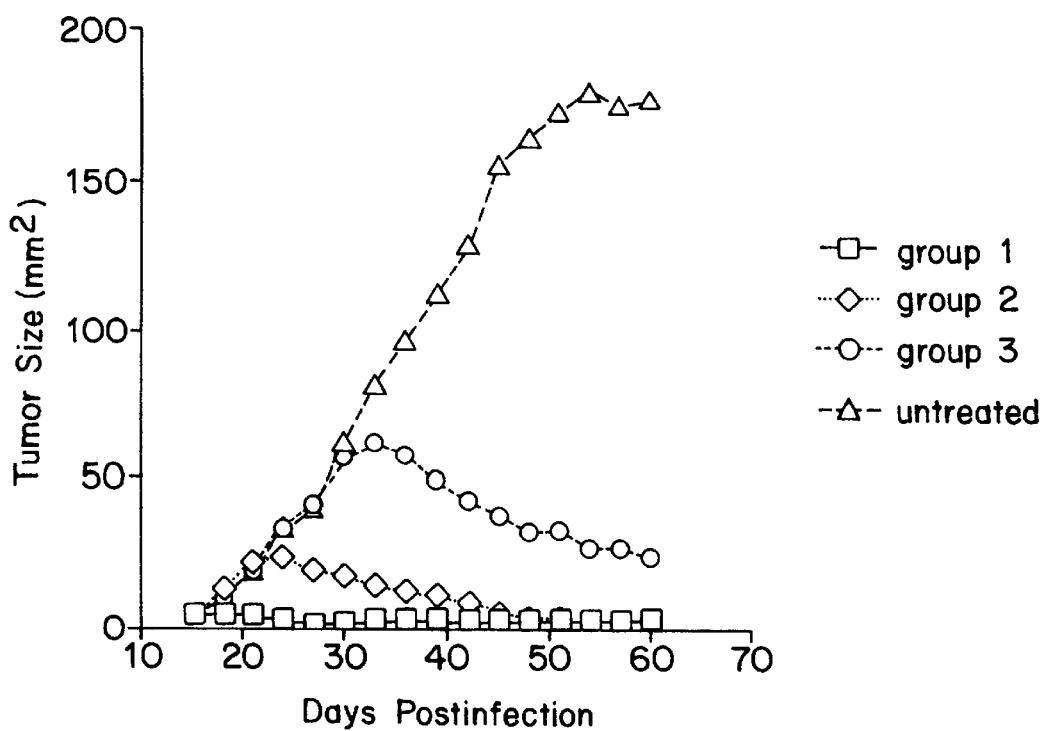
FIG. 3 is a graph depicting the effects of recombinant virus Ad5/IFN on growth of established MDA-MB-435 breast carcinoma in athymic nude mice. The mice were treated with recombinant virus at 3-day intervals starting at day 15 post infection for group 1, day 21 post infection for group 2, and 27 days post infection for group 3.

Virus was injected at 3-day intervals directly into established tumors beginning at days 15, 21, and 27 after the final inoculum. Regression occurred even in the large tumors (40 mm$^2$). In mice from group 1 (15 days) and group 2 (21 days) there was complete regression, whereas in the case of more advanced tumors, group 3 (27 days), there was complete regression in two of the five animals and partial regression in the other three. The rate of tumor regression is depicted in FIG. 3.

When Ad5/wt or Ad5/lfu was injected 20 days after transplantation of the xenograft a significant decrease in tumor progression occurred. This was significantly less effective, however, than using Ad5/IFN. Treatment with IFN-con$_1$ itself at clinically relevant doses at 3-day intervals (100,000 units/mL) resulted in a significant decrease in growth, although this decrease was less than with any of the other treatments. These results are depicted in FIG. 4.

EXAMPLE 4

This example describes a study wherein K562 cells, a myelogenous leukemic cell line known to form large tumors in vivo (within one hour of transplantation into athymic nude mice) and known to be quite resistant to IFN in vitro (see Example 6) were treated with various recombinant viruses shortly after transplantation.

K562 cells were injected into the thigh area of 3- to 4-week-old female athymic BALB/c mice (Harlan-Sprague-Dawley) at a concentration of $5\times10^5$ cells in 100 μl PBS per mouse. On the following day, either Ad5/wt ($1\times10^8$pfu), Ad5/IFN ($1\times10^8$pfu), Ad5/lfu ($1\times10^8$ pfu), or PBS (100 μl) were injected into the same area, and then tumor growth evaluated for 50 days.

There was complete lack of growth when Ad5/IFN was injected into the area 24 hours after tumor cell injection (FIG. 5). And, although there was significant inhibition of growth rate for both Ad5/lfu and Ad5/wt, it was not as pronounced as was the case of MDA-MB-435 cells.

EXAMPLE 5

This example describes a study wherein RPMI 1846 cells, a fast growing hamster melanoma which develops into a tumor in Syrian hamsters, were treated with various recombinant viruses shortly after transplantation.

Female Golden Syrian hamsters (Harlan-Sprague-Dawley) (65–75 gms; 5–6 weeks old) were anesthetized by injection of 80–100 mL ketamine HCl at a concentration of 100 mg/mL. RPMI 1846 melanoma cells ($10^5$) in 100 μl of medium were injected s.c. into the thigh region of a hamster using a 1-mL syringe and 22-gauge needle. On the following day, either Ad5/wt ($1\times10^8$pfu), Ad5/IFN ($1\times10^8$pfu), Ad5/lfu ($1\times10^8$pfu), or PBS (100 μl) were injected into the same area, and then tumor growth evaluated for 25 days.

Figure 6:
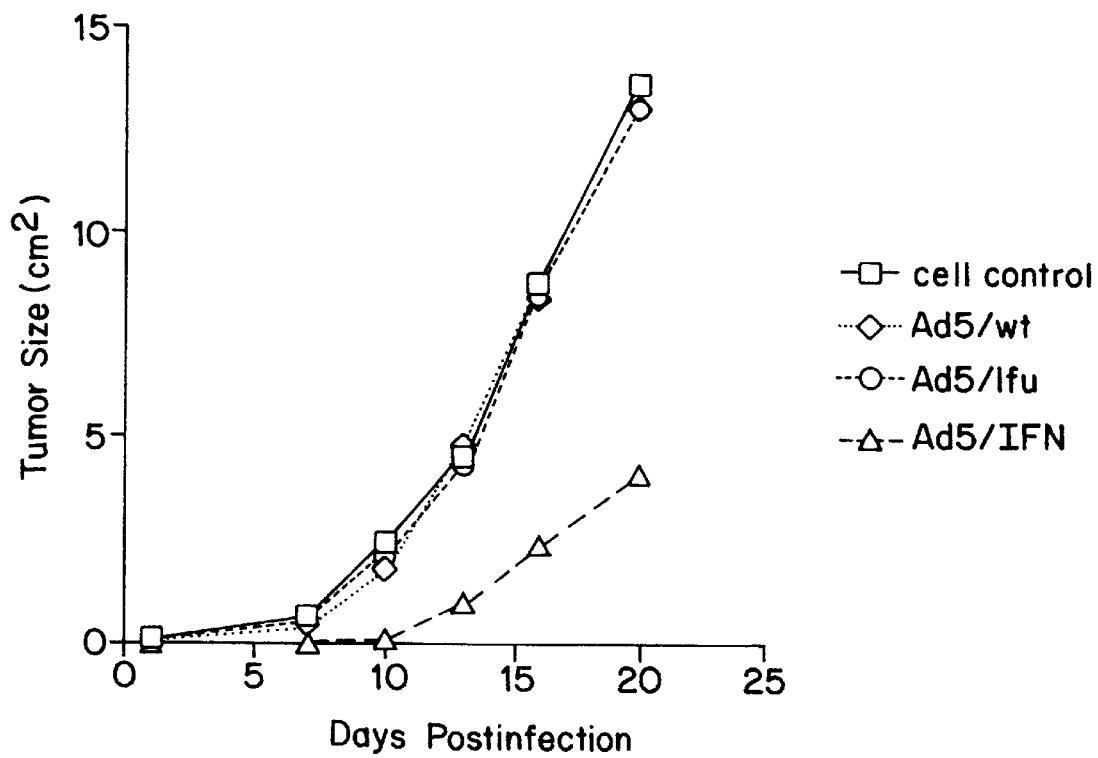
FIG. 6 is a graph depicting the effects of Ad5/wt, and recombinant viruses Ad5/lfu and Ad5/IFN on growth of RPMI 1846 melanoma cells in athymic nude mice. The mice were treated with the recombinant viruses on day 1 post infection.

As depicted in FIG. 6, only Ad5/IFN inhibited tumor growth. There was no significant difference between controls and Ad5/wt or Ad5/lfu. When the experiment was conducted on established tumors, Ad5/IFN did inhibit the development of the established tumor and temporarily inhibited growth, whereas Ad5/wt and Ad5/lfu had no effect.

EXAMPLE 6

This example describes a study wherein the in vitro effects of each of the recombinant adenovirus viruses on MDA-MB-435 cell growth, K562 cell growth, and RPMI 1846 cell growth was evaluated.

Figure 7:
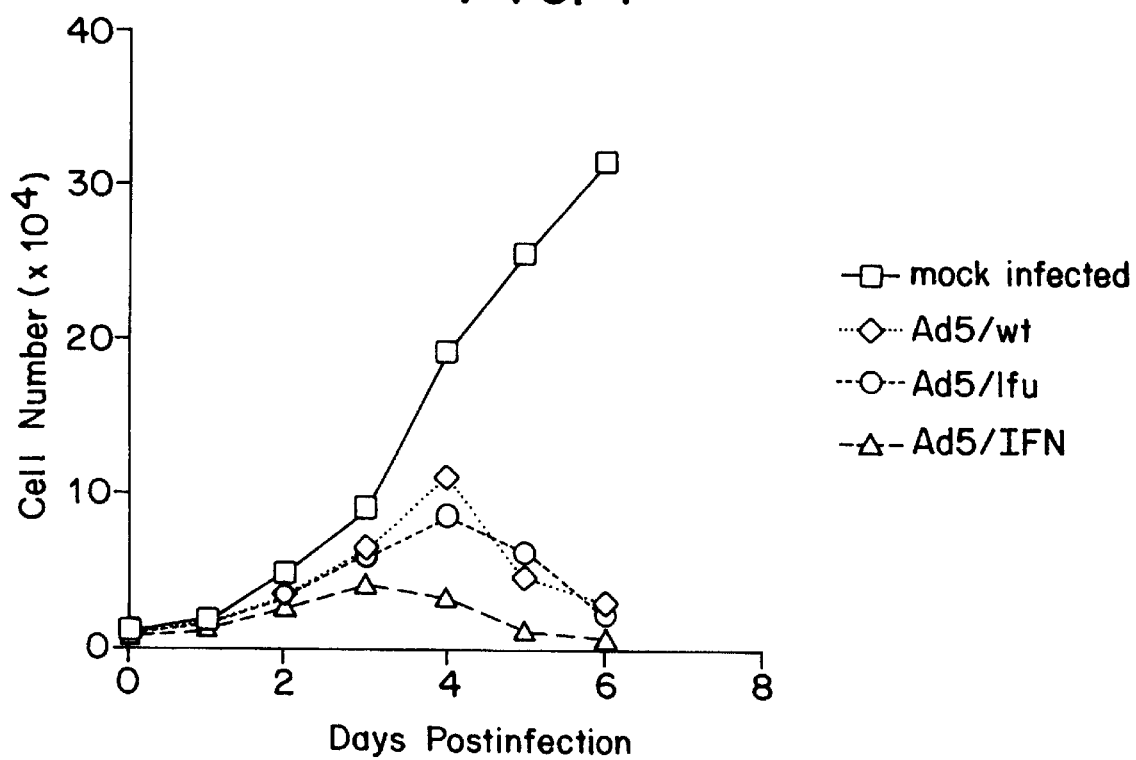
FIG. 7 is a graph depicting growth curve of MDA-MB-435 cells infected with Ad5/wt or recombinant viruses Ad5/lfu and Ad5/IFN. Ad5/wt, Ad5/lfu and Ad5/IFN were added 24 hours post infection.
Figure 8:
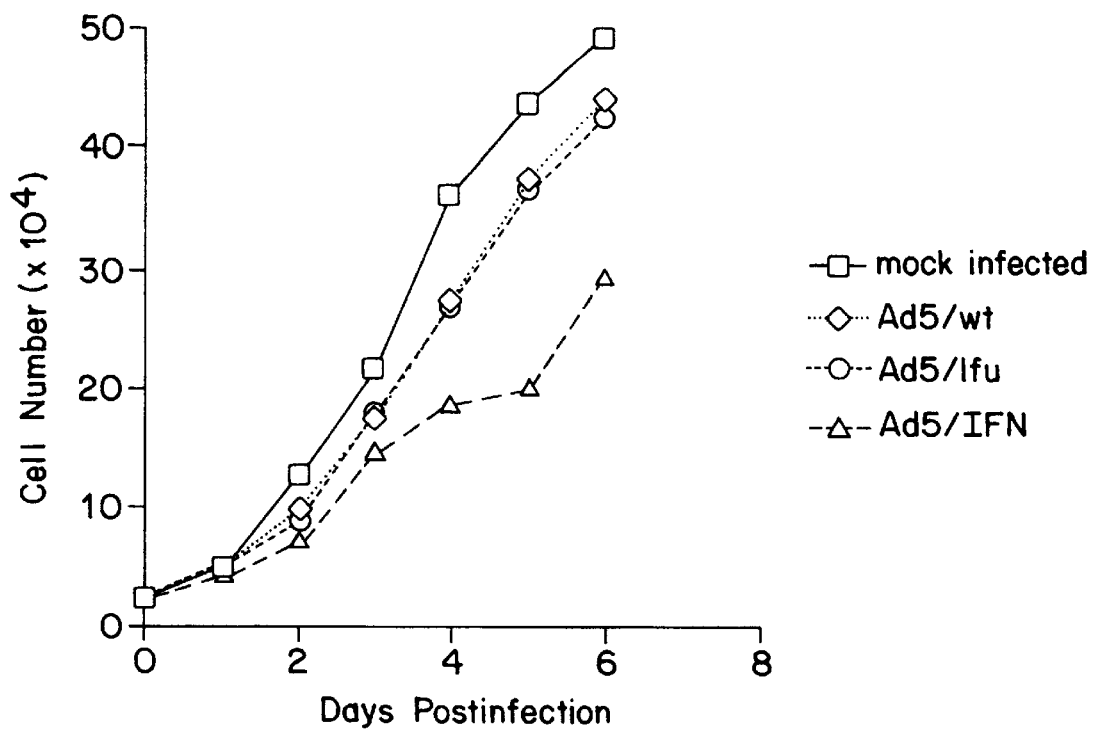
FIG. 8 is a graph depicting growth curve of K562 cells infected with Ad5/wt or recombinant viruses Ad5/lfu and Ad5/IFN. Ad5/wt, Ad5/lfu and Ad5/IFN were added 24 hours post infection.
Figure 9:
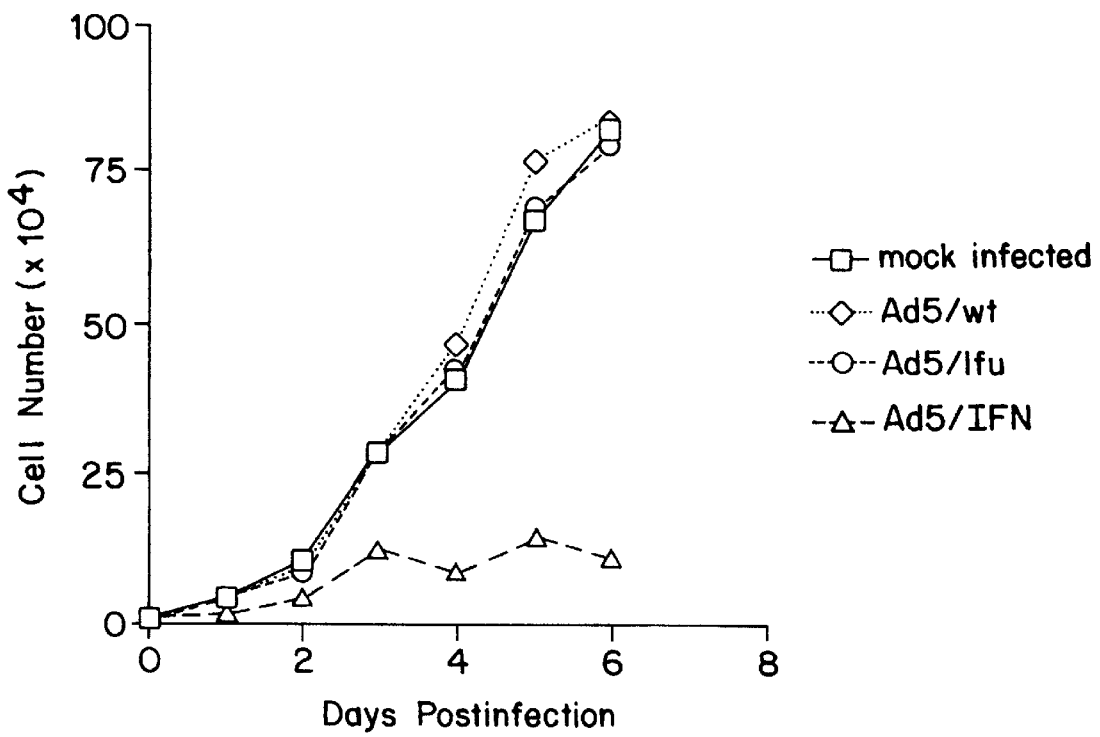
FIG. 9 is a graph depicting growth curve of RPMI 1846 cells infected with Ad5/wt or recombinant viruses Ad5/lfu and Ad5/IFN. Ad5/wt, Ad5/lfu and Ad5/IFN were added 24 hours post infection.

Each of the above identified cells were plated at a density of $1\times10^4$ cells per well in 48-well plates were infected with Ad5/wt, Ad5/lfu, and Ad5/IFN at multiplicity of infection (moi) of 100. FIG. 7 illustrates that all three viruses inhibited the growth of MDA-MB-435 cells and lysed the cells; importantly, however, Ad5/IFN was significantly ($P<0.001$) more potent than the other two viruses. FIG. 8 illustrates that K562 cells did not show cell lysis, and, although there appears to be a greater effect of Ad5/IFN than the other viruses, the difference is not significant ($P>0.05$), thus the in vitro data did not correlate with the in vivo results. The Ad5/IFN treatment of K562 was, however, significantly different ($P<0.005$) from the control. Finally, FIG. 9 illustrates that neither Ad5/wt or Ad5/lfu had any effect on RPMI 1846 cell viability; however, RPMI 1846 cells were very sensitive to Ad5/IFN.

EXAMPLE 7

In this example, the amount of IFN-con$_1$ being produced by infected cells was measured from 6 to 72 hours after infection in vitro every 6 hours. IFN-con$_1$ produced was determined by the inhibition of cytopathic effect assay with HeLa cells and vesicular stomatitis virus as challenge virus. Medium was collected at intervals between 6 and 72 hours after infection and tested. Human IFN standard (Namalwa Sendai, Ga 23-901-532) was used as a control. MDA-MB-435, RPMI 1846, and K562 all produced IFN-con$_1$. The amount produced varied slightly at each time point. MDA-MB-435 cells and RPMI 1846 cells produced between 40,000 and 60,000 units of IFN-con$_1$ per day for each $10^6$ cells. On the other hand, K562 cells produced between 5,000 and 20,000 units per day for each $10^6$ cells. All three cell lines are resistant to low levels of IFN (100–1000 units/mL) under growth conditions.

EXAMPLE 8

This example provides histological analysis of control and treated breast tumors. MDA-MB-435 tumor samples obtained from untreated control mice, and from recombinant virus-treated mice were dissected, fixed in formalin, and embedded in paraffin. Percentage of tumor necrosis was calculated on hematoxylin/eosin stained sections at ×400 magnification using a 10 mm×10 mm ocular grid on several representative cross sections of the tumor. Immunochemistry for the proliferation associated markers Ki-67 (clone MIB1, dilution 1:5; Oncogene Science) and PCNA (clone PC10, dilution 1:1000: Dako Inc.) and the tumor suppressor gene product p53 [Pab 1801, dilution 1:10, PB53-12 dilution 1:40, NovoCastra, Newcastle, U.K.] was performed on paraffin section using a microwave oven-based antigen retrieval before treatment as described; Orazi et al., *Mod. Pathol.*, 6:521–525 (1993).

Other proteins investigated by immunostaining in this study included apoptosis inhibitor oncoprotein Bcl-2 (clone 124, dilution 1:30; Dako), c-erb-2 oncoprotein (clone CB11, dilution 40; NovaCastra), and estrogen receptor (clone ERID5, dilution 1:50;AMAC, Westbrook, Me.). Following overnight incubation with the primary antibodies, the slides were stained with a biotin-conjugated goat anti-mouse antibody (30 min; Kirkegaard & Perry Laboratories) followed by peroxidase-conjugated streptavidin (30 mins; Kirkegaard & Perry Laboratories). The enzyme was developed with 3,3'-diaminobenzidine (Sigma). The results were expressed as a percentage of positively stained neoplastic cell nuclei. Apoptosis was measured by a nonisotopic, in situ DNA end-labeling (ISEL) technique (ApopTag; Oncor) applied to paraffin sections obtained from the same blocks used for immunostaining.

The results of histological analysis of the control and treated breast tumors is summarized in Table 1.

TABLE 1

| Treatment | # of samples | diameter | necrosis | p53 | Ki-67 |
|---|---|---|---|---|---|
| Ad5/IFN | 5 | 3.5 ± 0.4 mm | 57.2 ± 13.1% | 45.4 ± 3.8% | 60.0 ± 6.1% |
| Ad/wt | 4 | 5.5 ± 1.1 mm | 43.2 ± 16.3% | 49.7 ± 10.7% | 62.8 ± 17% |
| IFN | 3 | 7.6 ± 2.3 mm | 4.3 ± 1.2% | 82.7 ± 8.4% | 89.3 ± 3.5% |
| Untreated | 6 | 9.9 ± 2.3 mm | 19.8 ± 4.0% | 84.3 ± 4.0% | 84.4 ± 8.1% |

The results demonstrate that MDA-MB-435 tumor samples obtained from untreated control mice were characterized by less necrosis, stronger expression of p53 oncoprotein, and higher proliferative activity as measured by Ki-67 ($P<0.01$) and PCNA ($P<0.01$) immunostaining than the Ad5/IFN and Ad5/wt infected tumors. The decreased p53 expression in the Ad5/wt and Ad5/IFN treated tumors suggests a down-regulation of this tumor suppressor gene product which has been shown to be frequently involved in human breast cancer, especially in cases with aggressive clinical behavior. However, the down-regulation appears to be mainly a response to the adenovirus genome and not the IFN. Thus, the in vitro results correlate with the in vivo data, and suggest that tumor regression is due to an oncolytic effect of the virus that is significantly enhanced by the presence of the IFN-$con_1$ gene.

ISEL for fragmented DNA in the different sample groups showed similar results. This suggests that the regressive effects that are observed in the virus-infected specimens are not apoptosis-mediated but may be related to down regulation of p53. MDA-MB-435 cells were also estrogen-receptor negative and Bcl-2 negative.

These results suggest that the model might be applicable to human breast in a clinical situation. Ad5 is only slightly pathogenic to humans (common cold) and the IFN would be delivered to the site of the tumor by the virus. There would be high production of IFN at the site of the tumor, and IFN would be present at the site for several days. Viral oncolysis would lead to rapid tumor necrosis and IFN would retard the growth of surviving cells and enhance the necrotic event.

EXAMPLE 9

In this example, AAV/IFN-con vectors were constructed and recombinant virions used to infect a number of human tumor cells lines. The recombinant virion was constructed as described in Example 1; however, AAV vectors (pmMT-1 and pWP19) were used instead of the Ad5 adenovirus vector. The pmMT-1 AAV vector is under the control of an inducible promoter, the mouse metallothionein promoter. Thus, the system utilized will mimic the possible situation in humans in which one would not want to overproduce the cytokine because of possible side effects. Cells lines tested included HeLa (a cervical carcinoma cell line), Eskol (derived from a patient with hairy cell leukemia), and 293 (AD-5 transformed human primary embryonic kidney, ATCC, CRL 157). Each of the cell lines are resistant to IFN in vitro.

AAV/IFN-$con_1$ vector was added to $1\times10^5$ 293 cells, HeLa cells, and Eskol cells. Two to four hours later, cells were collected and suspended at $5\times10^3$ cells per 60×15 mm dish, at which time geneticin (G418) was added. Cultures were maintained in medium containing geneticin (G418) for 2 to 3 weeks with medium changes every 2 to 3 days until uninfected control dishes contained no viable cells. Clones were then isolated and grown to provide stock cultures.

The amount of IFN-$con_1$ being produced by each of the clones from different cell types was measured from 6 to 72 hours after infection in vitro every 6 hours as described in Example 7. It was determined that each of the tested cells lines produced IFN-$con_1$ at a low but steady level, and there was little variation of expression with time. 293 clones produced approximately 1000 U of IFN activity per $1\times10^6$ cells over a 24-hour period, HeLa cells produced 60–100 U of IFN activity per $1\times10^6$ cells and Eskol cells produced 60 U of IFN activity per $1\times10^6$ cells. The low constitutive levels of IFN-$con_1$ production may have been due to the leakiness of the metallothionein promoter. Because the cell lines were producing IFN-$con_1$ at low levels, the cell lines were tested to see whether they were now resistant to infection by virus. Transduced cell lines HeLa and 293 were completely resistant to VSV and EMC virus at an MOI of 0.1 Or 1.0 without the addition of exogenous IFN-$con_1$.

Regarding the effects of the AAV/IFN-$con_1$ vector on the growth rates of the infected cells themselves, there was no significant difference in the growth rates of the transduced cell lines compared to the parental cell lines.

Control or transduced cells were injected into the thigh area of 3- to 4-week-old female athymic BALB/c mice (Harlan-Sprague-Dawley) at a concentration of $2\times10^7$ cells in 100 μl PBS per mouse. Injection of control tumor cells resulted in palpable tumors within 7 to 14 days for each of the three cells lines, whereas the AAV/IFN-$con_1$ transduced Eskol and AAV/IFN-$con_1$ transduced 293 cells had no tumor formation even after 3 months (Table 2). In the case of HeLa cells, the tumors produced by the AAV/IFN-$con_1$ transduced cells were much smaller than those produced by the control cells.

TABLE 2

| Cell Type | 1 week | 2 weeks | 8 weeks |
|---|---|---|---|
| Eskol-control | 8/8 | 8/8 | 8/8 |
| Eskol-AAV/IFN | 0/8 | 0/8 | 0/8 |
| 293-control | 1/6 | 4/6 | 6/6 |
| 293-AAV/IFN | 0/6 | 0/6 | 0/6 |

TABLE 2-continued

| Cell Type | 1 week | 2 weeks | 8 weeks |
|---|---|---|---|
| HeLa-control | 0/6 | 6/6 | 6/6 |
| HeLa-AAV/IFN | 0/6 | 6/6 | 6/6 |

When established Eskol tumors (mice injected with Eskol cells and tumors allowed to grow for 7 days) were injected directly with $5\times10^6$ AAV/IFN-$con_1$-transduced 293 cells twice weekly, the established tumor regressed (Table 3). The regression was obvious one week after treatment, and by week 4 there was complete elimination of palpable tumor in three of the five mice. This complete regression was not seen in the case of treatment with IFN-$con_1$ alone, or a AAV/IFN-$con_1$ transduced Eskol cells, although the rate of growth was slower than control (phosphate buffered saline (PBS)) in the latter two cases.

TABLE 3

| Treatment | Day 0 | Day 7 | Day 14 | Day 28 |
|---|---|---|---|---|
| 293-AAV/IFN-$con_1$ | 0.506 | 0.864 | 1.24 | 0.8* |
| Eskol-AAV/IFN-$con_1$ | 0.826 | 2.17 | 2.84 | 3.66 |
| IFN-$con_1$ | 0.556 | 2.13 | 2.64 | 2.77 |
| Control (PBS) | 0.646 | 2.44 | 3.88 | 4.58 |

*by day 28, 3/5 mice in this group had no visible tumors

These results support the hypothesis that the AAV/IFN-$con_1$ gene acts as a tumor suppressor gene in vivo. The observation that addition of transduced AAV/IFN-$con_1$-transduced 293 cells to established tumors results in tumor regression suggests that the active component is a soluble protein, probably IFN-$con_1$. These results also suggest that therapy with the IFN-$con_1$ gene can be useful in the treatment of human cancers, both the hematopoietic type as well as solid tumors.

What is claimed is:

1. A nucleic acid construct comprising an expression control sequence and an human interferon consensus gene which is operatively linked to said expression control sequence.

2. A DNA sequence consisting of the sequence set forth in SEQ ID NO:4.

* * * * *

UNITED STATES PATENT AND TRADEMARK OFFICE
CERTIFICATE OF CORRECTION

PATENT NO. : 5,831,062
DATED : Nov. 3, 1998
INVENTOR(S) : Milton W. Taylor and Lawrence M. Blatt It is certified that error appears in the above-identified patent and that said Letters Patent is hereby corrected as shown below:

Column 7, line 12 - Sequence listing should read:
GACAAGGCCATGGTGG 3'

Column 7, line 45 - Sequence listing should read:
TTACCTCAAACTCATTCTCTTGGTAACCGTCGCGCTCTGATTC Signed and Sealed this Twenty-third Day of March, 1999

Attest:

Q. TODD DICKINSON

Attesting Officer

Acting Commissioner of Patents and Trademarks